United States Patent [19]

Katayama et al.

[11] 4,289,581

[45] Sep. 15, 1981

[54] MICROBICIDAL SLIMICIDE COMPOSITIONS FOR INDUSTRIAL USE

[75] Inventors: Sakae Katayama, Kobe; Osamu Umekawa, Takatsuki, both of Japan

[73] Assignee: Katayama Chemical Works Co., Ltd., Osaka, Japan

[21] Appl. No.: 22,955

[22] Filed: Mar. 23, 1979

[30] Foreign Application Priority Data

Apr. 5, 1978 [JP] Japan .................................. 53-40620
Apr. 11, 1978 [JP] Japan .................................. 53-43697

[51] Int. Cl.$^3$ .......................... D21D 3/00; C02F 1/50; A61K 31/385
[52] U.S. Cl. .................................. 162/161; 210/764; 424/277
[58] Field of Search .................... 162/161; 210/64, 62; 424/277; 71/67

[56] References Cited

U.S. PATENT DOCUMENTS 3,659,010 4/1972 Bader et al. ......................... 424/277
3,824,318 7/1974 Shema et al. ....................... 162/161

FOREIGN PATENT DOCUMENTS 51-82723 7/1976 Japan .
52-14294 4/1977 Japan .

OTHER PUBLICATIONS

McCutcheon, "Detergents & Emulsifiers", 1975 Annual, p. 241.
Abstract of Japanese 14294/1977.

*Primary Examiner*—Peter Chin
*Attorney, Agent, or Firm*—Hubbell, Cohen, Stiefel & Gross

[57] ABSTRACT

There disclose stable and non-aqueous microbicidal compositions which are useful for controlling slime in pulp and paper manufacturing processes and industrial cooling water systems and which comprise 4,5-dichloro-1,2-dithiol-3-one as the active ingredient, and specific surfactants and hydrophilic organic solvents.

13 Claims, No Drawings

MICROBICIDAL SLIMICIDE COMPOSITIONS FOR INDUSTRIAL USE

BACKGROUND OF THE INVENTION

1. Field of the Invention

This invention relates to microbicidal compositions for industrial use, and in particular to slime controlling compositions to be used in pulp and paper manufacturing processes and in industrial cooling water systems, in other words, compositions useful as microbicidal compositions to be used in water systems.

2. Description of the Prior Art

The active ingredient of the compositions of the present invention, namely 4,5-dichloro-1,2-dithiol-3-one, is known to have potent bactericidal and fungicidal activities (Japanese Patent Publication No. 14294/1977). Since this compound is hardly soluble in water, however, compositions in which said compound is made soluble in water are required in order that the compound may be utilized as slime controlling agent in paper manufacturing processes and in industrial cooling water systems. Consequently some compositions have been proposed which employ as surfactant a specific quaternary ammonium salt or a specific pyridinium salt (Japanese Patent Application Laid-Open No. 82723/1976). However, the compositions shown therein by way of examples contain said surfactant in an amount 2.5-5 times as much as that of the active ingredient and that in a water-containing solvent.

There are also known aqueous or nonaqueous compositions wherein a specific quaternary ammonium salt is added in an amount approximately equal to that of a certain active ingredient (methylenebisthiocyanate) which is effective as slime controlling agent useful also in paper manufacturing processes, in expectation of bactericidal activity of said ammonium salt itself (cf. Japanese Patent Publication No. 10927/1975 and No. 21319/1970); and aqueous or nonaqueous compositions including slimicidal ones, wherein nonionic surfactants are added in amounts almost equal to or smaller than those of active ingredients (cf. Japanese Patent Publications Nos. 23897/1973, 23902/1973, 38848/1973 and 21319/1970).

Whereas, as mentioned above, slime controlling compositions for use in paper manufacturing processes should desirably be water-soluble, the active ingredient may be water-insoluble but then the active ingredient is required to be capable of being well dispersed in the form of minute particles. It is of course required that the slime controlling composition should not be corrosive against the machinery, not adversely affect paper in respect of properties thereof, such as sizing degree, brightness, strength, color, etc., and not do any such harm to papermaking as decrease in freeness or in yield. what is more important is that the composition, when used at a necessary concentration, should not cause any foaming. The compositions for use in cooling water systems, too, are naturally required not to cause bubble formation and to have minimal adverse effect on the machinery.

DETAILED DESCRIPTION OF THE INVENTION

The present inventors have conducted intensive research on the preparation of compositions containing 4,5-dichloro-1,2-dithiol-3-one having the formula:

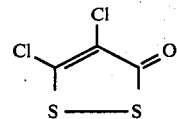

and have now succeeded in making novel and stable nonaqueous compositions.

The compositions of the present invention do not use water as solvent, but contain specific surfactants selected from among a very wide range of surfactants, and the compositions themselves are very stable. Moreover, the compositions, when used in water systems, allow the active ingredient to be dispersed in a very satisfactory manner so that it can show its bactericidal and fungicidal activities to the fullest. In addition, the amount of said specific surfactants to be added is extremely small from a common-sense standpoint, and therefore no foaming problem may arise from the addition of the surfactants. Furthermore, the compositions of the invention have such an advantage that the use thereof does not adversely affect the properties of paper.

Thus, according to the present invention, there are provided stable microbicidal compositions for industrial use which comprises 3-20 parts by weight of 4,5-dichloro-1,2-dithiol-3-one as active ingredient, at least 0.2 part by weight per 10 parts by weight of said active ingredient of a surfactant selected from the group consisting of N, N, N', N'-polyoxyethylene polyoxypropylene-ethylenediamines and alkylolamide type nonionic surfactants, and a sufficient amount of a hydrophilic organic solvent to make 100 parts by weight of the composition, said composition being substantially free from water.

The amount of the active ingredient, 4,5-dichloro-1,2-dithiol-3-one, in 100 parts by weight of the whole composition is generally 3-20, preferably 5-15, and more preferably 8-12 parts by weight. If the amount is excessively large, a crystalline precipitate may separate out during blending, storage or use. Conversely, if the amount is too small, the resulting composition will be disadvantageous from an economical standpoint.

"N, N, N', N'-polyoxyethylene polyoxypropylene-ethylenediamines" as used in the invention can be expressed as ethylenediamine adducts of ethylene oxide-propylene oxide block copolymers, which are surfactants and may be prepared by reacting ethylenediamine with propylene oxide and reacting the resultant with ethylene oxide in accordance with the conventional method. Such surfactant may be represented by the following formula:

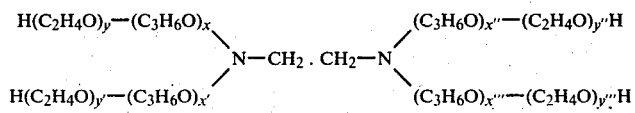

TETRONICS ® (Wyonddotte Chemical Corp., U.S.A.) and TETRONIC ® (Asahi Denka Kogyo K.K.) are mentioned as commercially available products of said surfactant.

In practicing the invention, a wide variety of N, N, N', N'-polyoxyethylene polyoxypropylene-ethylenediamines having variously different molecular weights, HLB (hydrophilic lipophilic balance) values, forms and other characteristics depending on the amounts specified as desired of ethylene oxide and propylene oxide added respectively and on the manner of combination of these can be used. Generally, however, those wherein the total molecular weight of the propylene oxide units is about 2,000-27,000 and the ethylene oxide unit content is 10-80 percent by weight based on the whole molecule are used.

The term "alkylolamide type nonionic surfactants" as used herein means fatty acid alkylolamides synthesized from fatty acids and alkylolamines. Preferred are the alkylolamides obtained by reaction of higher fatty acids having 8-18 carbon atoms and ethanolamine or diethanolamine. Those that are soluble in water are recommendable. Especially preferred fatty acid alkylolamides are those obtained by reaction of one mole of coconut oil fatty acid (a mixture of higher fatty acids derived from coconut oil) with one or two moles of diethanolamine. As commercially available products there are mentioned CONCENSATE P.A ® (Continental Chemical Co., U.S.A.), STATOAMF ® (Nippon Oil & Fats Co., Ltd., Japan) and PROFAN ® (Sanyo Chemical Ind. Ltd., Japan).

The amount of the surfactant specified herein and to be added is at least 0.2 part by weight per 10 parts by weight of the active ingredient, or at least 0.006 percent by weight based on the whole composition. The amount is generally 0.3 part by weight or more per 10 parts by weight of the active ingredient. In the case of an ethylene oxide-propylene oxide block copolymer-ethylenediamine adduct 0.3-1.0 part by weight thereof is preferred and in the case of an alkylolamide type nonionic surfactant 0.3-3.0 parts by weight thereof are preferred, per 10 parts by weight of the active ingredient. Sometimes the surfactant may amount to 2-8 parts by weight on the same basis. Larger amounts, though generally favorable for the active ingredient to be dispersed well in the organic solvent, are unfavorable because of possible foaming at the time of use.

It is essential that the hydrophilic organic solvent to be used according to the present invention is capable of dissolving the active ingredient as well as compatible or miscible with water, that, when used with the surfactant specified herein, said solvent gives a stable composition, and that, when the composition is added to water, said solvent facilitates dispersion of the composition. Suitable examples of the hydrophilic organic solvent are amides (dimethylformamide and diethylformamide), ethers (methyl cellosolve, ethyl cellosolve, phenyl cellosolve and diethylene glycol monomethyl ether), alcohols and glycols (isopropyl alcohol, diethylene glycol, dipropylene glycol and polypropylene glycol) and ketones (acetone and methyl isobutyl ketone). Combined use of two or more of these is possible. Among others are preferred, in view of stability of the resulting composition which also contains the surfactant and good dispersibility noted when the composition is added to water, dimethylformamide, methyl cellosolve, phenyl cellosolve, polyethylene glycol, diethylene glycol, diethylene glycol monomethyl ether and dipropylene glycol. In each case, the most preferable is dimethylformamide alone or in combination with one or more of the preferable solvents mentioned above.

These hydrophilic organic solvents may be of industrial grades. That is to say, they need not be absolutely anhydrous, but should be used in a substantially anhydrous state. Of course, water is never added to the composition.

The hydrophilic organic solvent generally amounts to less than about 95 percent by weight based on the composition.

In preparing the compositions of the present invention, conventional methods of dissolution and blending can be employed. Thus, for example, the active ingredient is dissolved in the hydrophilic organic solvent with stirring, and then, to the resulting solution, the surfactant specified herein is added, followed by stirring to yield a homogeneous composition. The order of dissolutions or blendings can naturally be reversed.

The composition of the present invention is used at concentrations depending upon the kind of industrial water (process water in paper and pulp making, cooling water, washing water, etc.), the state of attaching slime, the kinds of slime-forming bacteria, fungi and yeasts, etc.. Generally, concentrations of 5-50 ppm (the concentrations of the active ingredient being 0.25-10 ppm) are sufficient to inhibit the growth of microorganisms. In cases where bactericidal and fungicidal effects are to be achieved, the composition is used at concentrations of 10-100 ppm, preferably 30-50 ppm, with success.

More specifically, in paper making process, the composition of the present invention is added to the stuff box, the stock part of machine chest or the circulating part of white water in save-all, by a conventional continuous or impact feeding method. For instance, the impact feeding is conducted once to three times per day, taking 30 or 60 minutes per dosing. In cooling water system, the composition is added to e.g., the cooling pit, once with one portion for one to ten days in a quantity which gives an effective concentration for the total cooling water. Also, the composition can be added to the pulp slurry which is stored during stop of operation of paper making machine. In this case, the composition is dosed in one portion and in a quantity which is sufficient to give a necessary effective concentration.

The following examples will illustrate the invention more in detail.

EXAMPLES 1-24 and COMPARATIVE EXAMPLES 1-4

Various compositions were prepared according to the recipes specified in Tables 1 and 2 and following the procedure described hereinafter, and examined for their stability, dispersibility in water and foaming ability.

Thus, 4,5-dichloro-1,2-dithiol-3-one is dissolved in a solvent, and a surfactant is added in specified amounts. One hundred microliters (100 μl) of the resulting composition was pipetted and added dropwise to 100 cc of water in a glass colorimetry cell 25 mm in diameter and 300 mm in height. The stage in which the test composition was emulsified and dispersed in water was observed. After completion of the dropping, the mixture was shaken vigorously for 30 seconds and then allowed to stand, and the foaming power was evaluated in terms of the height of the remaining foam.

TABLE 1

Case where polyoxyethylenepolyoxypropylene-ethylenediamines were used as surfactants.

(Parts by weight)

| Example | Active ingredient | Surfactant | Dimethyl formamide | Diethylene glycol | Polyethylene glycol | Methyl Cellosolve | Phenyl Cellosolve | Diethylene glycol monoethyl ether |
|---|---|---|---|---|---|---|---|---|
| 1 | 10.0 | | 0.5 | 89.5 | — | — | — | — | — |
| 2 | 5.0 | M.W. 3700 | 1.5 | 93.5 | — | — | — | — | — |
| 3 | 15.0 | E.O. 30 wt % | 0.75 | 84.25 | — | — | — | — | — |
| 4 | 20.0 | | 1.0 | 79.0 | — | — | — | — | — |
| 5 | 10.0 | M.W. 3700 E.O. | 0.5 | 5.0 | 84.5 | — | — | — | — |
| 6 | 10.0 | 10 wt % | 0.5 | 5.0 | — | 84.5 | — | — | — |
| 7 | 10.0 | M.W. 3700 | 1.0 | — | — | — | 89.0 | — | — |
| 8 | 10.0 | E.O. | 0.5 | — | 49.5 | — | 40.0 | — | — |
| 9 | 10.0 | 20 wt % | 0.5 | — | — | 49.5 | 40.0 | — | — |
| 10 | 10.0 | M.W. 3700 E.O. | 1.0 | 50.0 | — | — | 39.0 | — | — |
| 11 | 10.0 | 40 wt % | 1.0 | — | — | — | 39.0 | 50.0 | — |
| 12 | 10.0 | M.W. 4000 | 0.5 | — | — | — | — | 89.5 | — |
| 13 | 10.0 | E.O. | 0.5 | — | 39.5 | — | — | 50.0 | — |
| 14 | 10.0 | 80 wt % | 0.5 | — | — | 39.5 | — | 50.0 | — |
| 15 | 5.0 | M.W. 6700 E.O. | 0.5 | — | — | — | — | — | 94.5 |
| 16 | 7.0 | 10 wt % | 0.5 | — | — | — | — | — | 92.5 |
| Comparative | | | | | | | | | |
| 1 | 25.0 | M.W. 6700 E.O. | 1.0 | 74.0 | — | — | — | — | — |
| 2 | 25.0 | 10 wt % | 10.0 | 65.0 | — | — | — | — | — |

Notes:
M.W. means the molecular weight of the hydrophobic portion (propylene oxide portion) in the polyoxyethylene polyoxypropylene-ethylenediamine, and E.O. means the proportion (weight percent) of the ethylene oxide portion to the whole molecule of said surfactant.

TABLE 2

Cases where coconut oil fatty acid diethanolamides were used as surfactants.

(Parts by Weight)

| Example | Active ingredient | Surfactant | Dimethyl formamide | Diethylene glycol | Polyethylene glycol | Methyl Cellosolve | Phenyl Cellosolve | Diethylene glycol monoethyl ether |
|---|---|---|---|---|---|---|---|---|
| 17 | 5 | 1.0* | 94 | — | — | — | — | — |
| 18 | 10 | 1.0** | 89 | — | — | — | — | — |
| 19 | 20 | 3.0** | 77 | — | — | — | — | — |
| 20 | 10 | 1.0** | 5 | 84 | — | — | — | — |
| 21 | 10 | 1.0* | 20 | — | 69 | — | — | — |
| 22 | 10 | 1.0** | 50 | — | — | 39 | — | — |
| 23 | 5 | 1.0* | — | 84 | — | — | — | — |
| 24 | 5 | 1.0** | — | 94 | — | — | — | — |
| Comparative | | | | | | | | |
| 3 | 25 | 1.0* | 74 | — | — | — | 10 | — |
| 4 | 25 | 10.0** | 65 | — | — | — | — | — |

Notes:
*denotes 1:1 type, i.e. reaction product of coconut oil fatty acid with diethanolamine in a molar ratio of 1:1, product of Sanyo Chemical Industries, Ltd., "Profan 1281" by trade name.
**denotes 1:2 type, i.e. reaction product of coconut oil fatty acid with diethanolamine in a molar ratio of 1:2, product of Sanyo Chemical Industries, Ltd., "Profan 1281 Extra" by trade name.

The compositions of Examples 1–24 shown in the above tables all were rapidly dispersed in water in an emulsified state after addition, presenting a uniform and good dispersion state in a short time. On the contrary, the compositions of Comparative Examples 1–4 upon addition caused precipitation of fine crystals of 4,5-dichloro-1,2-dithiol-3-one, and never gave uniform dispersions.

Concerning the forming phenomenon, such a phenomenon could not be observed at all with the compositions of Examples 1, 3–6, 8, 9, 12–14, 16, 18, 20, 22 and 24 and of Comparative Example 3. The compositions of Examples 2, 7, 10, 11, 15, 17, 19, 21 and 23 and of Comparative Example 1, when shaken, formed foam, but the foam, on standing, disappeared immediately. In the cases of Comparative Examples 2 and 4, foam remained and had a height of about 10 mm even after 15 seconds of standing.

Furthermore, the compositions of Examples 1-24 could be stored for more than 3 months without any change in their good state of dispersion; no tendency was noted toward separation or precipitation of crystals or the like.

EXAMPLES 25-26

The microbicidal compositions of Examples 3 and 21 were each tested to see their possible influence on the properties of paper.

A pulp was beaten according to the method employed in JIS P 8210 and the pulp concentration adjusted to 3%. A size ("SizePine E" by trade name, product of Arakawa Kagaku Kogyo K.K.) was added in an amount of 0.5% (as solid) based on the pulp, and the pH adjusted to 4.0 with aluminum sulfate. After 5 minutes of stirring and 10-fold dilution with water, the microbicidal composition was added so that each concentration specified in Table 3 might be attained. After standing for 5 minutes, paper specimens were made according to JIS P 8209 and tested for their properties by the conventional methods. The results are shown in Table 3.

EXAMPLE 29

The following test was made in a petrochemical plant equipped with a cooling tower system in which 400 tons of water was under circulation at a rate of 2,000 tons/hour.

The composition of Example 14 was added to the circulating water near the intake of the cold water pit so that a concentration of 50 ppm might result in said system. The addition caused decrease in number of bacteria from $5.0 \times 10^6$/ml before the addition to $1.0 \times 10^2$/ml after the addition. One week later, slime was no more formed, accordingly the cooling efficiency hardly decreased but the number of bacteria amounted to $1.0 \times 10^6$/ml. Therefore, the same composition was again added to a concentration of 50 ppm. Thereafter the addition of 50 ppm was repeated at hourly intervals for 3 months. Any trouble at least due to slime formation, such as choking or blocking of the heat exchanger or decrease in cooling efficiency, did not arise at all.

EXAMPLE 30

A test similar to that of Example 29 was made in a petrochemical plant equipped with a cooling tower system in which 300 tons of water was under circulation at a rate of 2,000 tons/hour.

The composition of Example 20 was added to the

TABLE 3

| Composition | Test method Concentration (ppm) | Brightness JIS P 8123 (%) | Breaking length JIS P 8113 (km) | Bursting strength JIS P 8112 (kPa) | Folding endurance JIS P 8115 (times) | Tearing strength JIS P 8116 (mN) | Sizing degree JIS P 8122 (sec) |
|---|---|---|---|---|---|---|---|
| Example 3 | 0 | 81.5 | 4.76 | 3.00 | 780 | 54.0 | 12.5 |
|  | 10 | 81.5 | 4.70 | 2.96 | 760 | 53.3 | 12.3 |
|  | 50 | 81.0 | 4.65 | 3.05 | 780 | 53.9 | 12.6 |
|  | 100 | 81.8 | 4.75 | 3.02 | 780 | 53.9 | 12.0 |
| Example 21 | 0 | 80.4 | 3.28 | 2.20 | 940 | 41.6 | 12.6 |
|  | 10 | 80.1 | 3.76 | 2.20 | 880 | 48.0 | 12.2 |
|  | 50 | 80.4 | 3.76 | 2.21 | 900 | 44.8 | 12.4 |
|  | 100 | 80.6 | 3.78 | 2.28 | 1000 | 41.6 | 12.1 |

It is clear from the results in Table 3 that the compositions of Examples 3 and 21 have no influence upon the properties of paper at a concentration as high as 100 ppm. Foaming was never promoted by the addition of the compositions of the present invention.

EXAMPLES 27-28

In a certain paper mill, in the white water circulating system of a paper machine for making wood free paper, especially on the deflector under the wire cloth, on the walls of the seveall and on the walls of the drum screen, pink slime mainly composed of Flavobacterium species was formed in large quantities, and a great number of pink spots appeared on the paper surface. In a short time, this made it necessary to do washing with water or a bleaching liquor. Here, after the washing, either of the microbicidal compositions of Examples 1 and 20 was injected into the flow of stock suspension in the machine chest for consecutive 8 hours daily so that a concentration of 10 ppm might be obtained. By these additions, pink slime formation was completely stopped, and spots on the product then hardly appeared. Naturally, the addition of the compositions of the invention did not cause foaming.

circulating water near the intake of the cold water pit so that a concentration of 50 ppm might result in said system. The addition caused decrease in number of bacteria from $6.0 \times 10^5$/ml before the addition to $2.0 \times 10^2$/ml after the addition. One week later, slime was no more formed, accordingly the cooling efficiency hardly decreased, but the number of bacteria amounted to $1.0 \times 10^6$/ml. Therefore, the same composition was again added to a concentration of 50 ppm. Thereafter the addition of 50 ppm was repeated at hourly intervals for 3 months. Any trouble at least due to slime formation, such as choking of the heat exchanger or decrease in cooling efficiency, did not arise at all.

What is claimed is:

1. A stable microbicidal slimicide composition for industrial use which comprises 3-20 parts by weight of 4,5-dichloro-1,2-dithiol-3-one as active ingredient, at least 0.2 part by weight per 10 parts by weight of said active ingredient of a surfactant selected from the group consisting of N,N,N',N'-polyoxyethylene polyoxypropylene-ethylenediamines and alkylolamides type nonionic surfactants, and a sufficient amount of a hydrophilic organic solvent consisting essentially of a solvent selected from the group consisting of dimethylformamide, methyl cellosolve, phenyl cellosolve, diethylene glycol, dipropylene glycol, diethylene glycol monomethyl ether, and mixtures thereof to make 100 parts by weight of the composition, said composition being substantially free from water.

2. The composition of claim 1, wherein said hydrophilic organic solvent is dimethylformamide.

3. The composition of claim 1, wherein said hydrophilic organic solvent is diethylene glycol monomethyl ether.

4. The composition of any one of claims 1, 2 or 3, wherein said polyoxyethylene polyoxypropylene-ethylenediamine is present in an amount of 0.3–1.0 part by weight per 10 parts by weight of said active ingredient.

5. The composition of any one of claims 1, 2 or 3, wherein said polyoxyethylene polyoxypropylene-ethylenediamine is present in an amount of 0.5–1.0 part by weight per 10 parts by weight of said active ingredient.

6. The composition of any one of claims 1, 2 or 3, wherein said alkylolamide type nonionic surfactant is present in an amount of 0.3–3.0 parts by weight per 10 parts by weight of said active ingredient.

7. The composition of any one of claims 1, 2 or 3, wherein said alkylolamide type nonionic surfactant is present in an amount of 0.5–2.0 parts by weight per 10 parts by weight of said active ingredient.

8. The composition of any one of claims 1, 2 or 3, wherein said active ingredient is present in an amount of 8–12 parts by weight per 100 parts by weight of said composition.

9. The composition of any one of claims 1, 2 or 3, wherein said active ingredient is present in an amount of 10 parts by weight per 100 parts by weight of said composition.

10. The composition of claim 1, wherein said alkyloamide type nonionic surfactant is a fatty acid diethanolamide.

11. The composition of claim 10, wherein said fatty acid diethanolamide is a product of the reaction of one mole of a fatty acid and one or two moles of diethanolamine.

12. The composition of claim 11, wherein said fatty acid diethanolamide is a product of the reaction of one mole of coconut oil fatty acid with one or two moles of diethanolamine.

13. In a method for controlling slime formation in wood pulp or paper manufacture, having a water system the improvement comprising adding a slimicide composition to said water system which is composed of 3–20 parts by weight of 4,5-dichloro-1,2-dithiol-3-one as active ingredient, at least 0.2 part by weight per 10 parts by weight of said active ingredient of a surfactant selected from the group consisting of N,N,N′,N′-polyoxypropylene polypropylene-ethylenediamines and alkylolamides type nonionic surfactants, and a sufficient amount of a hydrophilic organic solvent consisting essentially of a solvent selected from the group consisting of dimethylformamide, methyl cellosolve, phenyl cellosolve, diethylene glycol, dipropylene glycol, diethylene glycol monomethyl ether, and mixtures thereof to make 100 parts by weight of the composition, said composition being substantially free from water.

* * * * *

UNITED STATES PATENT AND TRADEMARK OFFICE
CERTIFICATE OF CORRECTION

PATENT NO. : 4,289,581

DATED : September 15, 1981

INVENTOR(S) : Sakae Katayama, et al.

It is certified that error appears in the above—identified patent and that said Letters Patent is hereby corrected as shown below:

On the Cover Page, the Assignee should be changed from "Katayama Chemical Works Co., Ltd., Osaka, Japan" to read -- Katayama Chemical Works Co., Ltd., Osaka, Japan and Yoshitomi Pharmaceutical Industries, Ltd., Osaka, Japan --.

Col. 1, line 56: "what is more" should read -- What is more --.

Col. 10, line 21: "-polyoxypropylene polypropylene-ethylene-diamines" should read -- polyoxyethylene polyoxypropylene-ethylenediamines --.

Signed and Sealed this

Nineteenth Day of January 1982

[SEAL]

Attest:

Attesting Officer

GERALD J. MOSSINGHOFF

Commissioner of Patents and Trademarks